US012767682B2

(12) United States Patent
Jennewein et al.

(10) Patent No.: US 12,767,682 B2
(45) Date of Patent: Oct. 20, 2026

(54) PROCESS FOR PURIFYING SIALYLATED OLIGOSACCHARIDES

(71) Applicant: Chr. Hansen A/S, Hoersholm (DK)

(72) Inventors: Stefan Jennewein, Bad Honnef (DE); Markus Helfrich, Bad Hoenningen (DE); Benedikt Engels, Bad Honnef (DE)

(73) Assignee: Chr. Hansen A/S, Hoersholm (DK)

(*) Notice: Subject to any disclaimer, the term of this patent is extended or adjusted under 35 U.S.C. 154(b) by 0 days.

(21) Appl. No.: 18/417,034

(22) Filed: Jan. 19, 2024

(65) Prior Publication Data

US 2024/0199673 A1 Jun. 20, 2024

Related U.S. Application Data

(62) Division of application No. 16/642,329, filed as application No. PCT/EP2018/073178 on Aug. 29, 2018, now Pat. No. 11,912,735.

(30) Foreign Application Priority Data

Aug. 29, 2017 (EP) .................................... 17188280

(51) Int. Cl.

| | |
|---|---|
| ***C07H 1/06*** | (2006.01) |
| ***A23L 33/00*** | (2016.01) |
| ***A23L 33/125*** | (2016.01) |
| ***A23L 33/135*** | (2016.01) |
| *C07H 3/06* | (2006.01) |

(52) U.S. Cl.

CPC .............. *C07H 1/06* (2013.01); *A23L 33/125* (2016.08); *A23L 33/135* (2016.08); *A23L 33/30* (2016.08); *C07H 3/06* (2013.01)

(58) Field of Classification Search

CPC .... C07H 1/06; C07H 1/08; C07H 3/06; A23L 1/30; A23L 1/09; A23L 33/30; A23L 33/135; A23L 33/125

USPC ....................................... 536/127; 514/123.1

See application file for complete search history.

(56) References Cited

U.S. PATENT DOCUMENTS

| | | | | |
|---|---|---|---|---|
| 7,521,212 | B1 | 4/2009 | Samain et al. | |
| 9,611,285 | B2 | 4/2017 | Parkot et al. | |
| 10,377,787 | B2 | 8/2019 | Jennewein | |
| 10,435,427 | B2 | 10/2019 | Jennewein | |
| 11,582,994 | B2 * | 2/2023 | Jennewein ............... | C12N 9/12 |
| 2004/0185146 | A1 | 9/2004 | Pelletier et al. | |
| 2010/0143535 | A1 | 6/2010 | Motoshima et al. | |
| 2011/0300584 | A1 | 12/2011 | Huefner et al. | |
| 2012/0021467 | A1 | 1/2012 | Zhang et al. | |
| 2014/0024820 | A1 | 1/2014 | Parkot et al. | |
| 2015/0183814 | A1 | 7/2015 | Schroven et al. | |
| 2015/0320778 | A1 | 11/2015 | Chow et al. | |
| 2016/0186223 | A1 | 6/2016 | Jennewein | |
| 2016/0237104 | A1 | 8/2016 | Jennewein et al. | |
| 2016/0333042 | A1 | 11/2016 | Jennewein | |
| 2019/0177352 | A1 | 6/2019 | Jennewein | |
| 2019/0292211 | A1 | 9/2019 | Jennewein et al. | |
| 2019/0382737 | A1 | 12/2019 | Huefner et al. | |
| 2020/0308211 | A1 | 10/2020 | Jennewein et al. | |

FOREIGN PATENT DOCUMENTS

| | | | |
|---|---|---|---|
| CN | 102154163 | A | 8/2011 |
| CN | 105532883 | A | 5/2016 |
| EP | 2479263 | B1 | 11/2013 |
| EP | 2845905 | A1 | 3/2015 |
| EP | 3111942 | A1 | 1/2017 |
| EP | 3315610 | A1 | 5/2018 |
| EP | 2896628 | B1 | 9/2018 |
| EP | 3450443 | A1 | 3/2019 |
| FR | 2907687 | A1 | 5/2008 |
| JP | S59184197 | A | 10/1984 |
| JP | H08283162 | A | 10/1996 |
| JP | 2001514865 | A | 9/2001 |
| JP | 2001502005 | | 5/2005 |
| JP | 2014506474 | A | 3/2014 |
| JP | 2014513986 | A | 6/2014 |
| JP | 2016535724 | A | 11/2016 |
| JP | 2017509346 | A | 4/2017 |
| KR | 101580348 | | 1/2016 |
| TW | 201249349 | A | 12/2012 |
| WO | 9815581 | A1 | 4/1998 |
| WO | 9908511 | A1 | 2/1999 |
| WO | 2004032639 | A1 | 4/2004 |
| WO | 2007101862 | A1 | 9/2007 |
| WO | 2009008362 | A1 | 1/2009 |
| WO | 2009113861 | A2 | 9/2009 |

(Continued)

OTHER PUBLICATIONS

Albermann, Christoph, et al., "Synthesis of the milk oligosaccharide 2'-fucosyllactose using recombinant bacterial enzymes." Carbohydrate research, (2001), vol. 334(2): 97-103.

(Continued)

*Primary Examiner* — Ganapathy Krishnan

(74) *Attorney, Agent, or Firm* — Kelly Reynolds; Eric J. Fechter

(57) ABSTRACT

Disclosed is a method for purifying sialylated oligosaccharides from a fermentation broth, cell-lysate or biocatalytic reaction mixture for obtaining high amounts of desired sialylated oligosaccharides in high purity. The method is particular suitable for the large-scale economic purification of sialylated human milk oligosaccharides (such as 3'-sialyllactose, 6'-sialyllactose or sialylated lacto-N-tetraose derivatives) from microbial fermentation, using recombinant bacterial cells or yeast cells. The obtained material is of high purity and can be used for food or medical application such like medical nutrition products, infant formula, dietary supplements, general nutrition products (e.g. dairy drinks).

7 Claims, 7 Drawing Sheets

(56) References Cited

FOREIGN PATENT DOCUMENTS

| | | | | |
|---|---|---|---|---|
| WO | 2010070104 A1 | 6/2010 | | |
| WO | 2010106320 A2 | 9/2010 | | |
| WO | 2010115935 A1 | 10/2010 | | |
| WO | 2011100979 A1 | 8/2011 | | |
| WO | 2011136647 A1 | 11/2011 | | |
| WO | 2011150939 A1 | 12/2011 | | |
| WO | 2012069415 A1 | 5/2012 | | |
| WO | 2012069416 A1 | 5/2012 | | |
| WO | 2012092155 A1 | 7/2012 | | |
| WO | 2012097950 A1 | 7/2012 | | |
| WO | WO 2012/092160 A2 * | 7/2012 | ............... | A23L 1/29 |
| WO | 2012112777 A2 | 8/2012 | | |
| WO | 2012156273 A1 | 11/2012 | | |
| WO | 2012156898 A1 | 11/2012 | | |
| WO | 2013185780 A1 | 12/2013 | | |
| WO | 2014075680 A1 | 5/2014 | | |
| WO | 2014086373 A1 | 6/2014 | | |
| WO | 2014094783 A1 | 6/2014 | | |
| WO | 2014100126 A1 | 6/2014 | | |
| WO | 2014100191 A1 | 6/2014 | | |
| WO | 2015049331 A1 | 4/2015 | | |
| WO | 2015071389 A1 | 5/2015 | | |
| WO | 2015106943 A1 | 7/2015 | | |
| WO | 2015150328 A1 | 10/2015 | | |
| WO | 2015164021 A1 | 10/2015 | | |
| WO | 2016086947 A1 | 6/2016 | | |
| WO | 2017043382 A1 | 3/2017 | | |
| WO | 2017101953 A1 | 6/2017 | | |
| WO | 2017101958 A1 | 6/2017 | | |
| WO | 2017103019 A1 | 6/2017 | | |
| WO | 2017152918 A1 | 9/2017 | | |
| WO | 2019020707 A1 | 1/2019 | | |
| WO | 2019043029 A1 | 3/2019 | | |

OTHER PUBLICATIONS

Dusseault et al., "Evaluation of alginate purification methods: Effect on polyphenol, endotoxin, and protein contamination," J Biomed Mater Res, 2006, 76A:243-251.

Fierfort, Nicolas, and Eric Samain. "Genetic engineering of *Escherichia coli* for the economical production of sialylated oligosaccharides." Journal of biotechnology, (2008), vol. 134, No. 3-4: 261-265.

Gura, Trisha. "Nature's first functional food." Science, (2014), vol. 345, No. 6198: 747-749.

International Search Report of International Patent Application No. PCT/EP2018/073178 dated Jan. 8, 2019.

Janstcher-Krenn et al., "The human oligosaccharide disialyllacto-N-tetraose prevents necrotising enterocolitis in neonatal rats," Gut, 2012, 61(10): 1-17.

Machine translation of CN102154163, Aug. 17, 2011, 6 pages.

Miyazaki, Tatsuo, et al., "Enzymatic synthesis of lacto-N-difucohexaose I which binds to Helicobacter pylori." In Methods in enzymology, 480: 511-524. Academic Press, 2010.

Morrow, Ardythe L., et al., "Human milk oligosaccharides are associated with protection against diarrhea in breast-fed infants." The Journal of pediatrics, (2004), 145(3): 297-303.

Murata, Takeomi, et al., "Facile enzymatic conversion of lactose into lacto-N-tetraose and lacto-N-neotetraose." Glycoconjugate journal, (1999), 16(3): 189-195.

Separation and Purification Technology in the Filed of Biotechnology—Review, Chemistry and Biology, 1988, 26(12):842-849.

Priem B et al., Glycobiology. 2002, vol. 12(4), pp. 235-240.

Drouillard S et al., Carbohydrate Research. 2010, vol. 345(10), pp. 1394-1399.

Yukijirushi Niyuugiyou KK, 1984, Machine translation of abstract of JPS59184197A.

Baumgartner et al., 2013, Microbial Cell Factories, 12, 40, 1-13.

Bode et al., 2012, Adv. Nutr., 3, 383S-391S.

Bode, 2012, Glycobiology, 22, 9, 1147-1162.

International Search Report of PCT/EP2018/083973 dated Feb. 1, 2019.

EU Regulation 2016-127.

Kemp et al., 2016, Drying Technology, 34, 7 830-842.

Kunz et al., 2017, McGuire ed., Prebiotics and Probiotics in Human Milk, 3-16.

Lee et al., 2012, Microbial Cell Factories, 11, 48, 1-10.

Thurl et al., 217, Nutrition Reviews, 75, 11, 920-933.

US CFR 21 107.100, up to date as of Apr. 16, 2026, 1-2.

Wisniewski, 2015, 45th International Conference on Environmental Systems, 1-46.

McGuire; 2017, Prebiotics and Probiotics in Human Milk_ Origins and Functions of Milk-Borne Oligosaccharides and Bacteria pp. 1-508.

* cited by examiner

3'-Sialyllactose

6'-Sialyllactose

PROCESS FOR PURIFYING SIALYLATED OLIGOSACCHARIDES

CROSS-REFERENCE TO RELATED APPLICATIONS

This application is a divisional of U.S. patent application Ser. No. 16/642,329, filed Feb. 26, 2020, which is a National Stage entry of International Application No. PCT/EP2018/073178, filed Aug. 29, 2018, which claims priority to European Patent Application No. 17188280.6, filed Aug. 29, 2017.

FIELD

The present invention relates to the purification of sialylated oligosaccharides. More specifically, the present invention concerns the purification of sialylated oligo-saccharides, in particular of sialylated human milk oligosaccharides (sHMOs), from a fermentation broth, a cleared cell lysate or a reaction mixture.

BACKGROUND

Human milk is a complex mixture of carbohydrates, fats, proteins, vitamins, minerals and trace elements. Carbohydrates are by far the most abundant fraction, which can be divided further into lactose and more complex oligosaccharides, the so-called human milk oligosaccharides (HMOs). Whereas lactose is used as an energy source, the complex oligosaccharides are not metabolized by the infant. The fraction of complex oligosaccharides accounts for up to 10% of the total carbohydrate fraction and probably consists of more than 150 different oligosaccharides. The occurrence and concentration of these complex oligosaccharides are specific to humans and thus cannot be found in large quantities in the milk of other mammals, such as domesticated dairy animals.

The presence of these complex oligosaccharides in human milk has been known for a long time and the physiological functions of these oligosaccharides have been the subject of medical research for many decades (Gura, T. (2014) *Science* 345: 747-749; Kunz, C. & Egge, H. (2017) In: Prebiotics and Probiotics in Human Milk. Eds. McGuire, M. K; McGuire, M. A. & Bode, L. Elsevier, London pp. 3-16). For some of the more abundant HMOs, specific functions have already been identified (Bode, L. (2012) *Glycobiology* 22: 1147-1162.; Bode, L. and Jantscher-Krenn, E. (2012) *Adv. Nutr.* 3: 383S-391 S; Morrow et al. (2004) *J. Pediatr.* 145: 297-303).

The limited supply of individual HMOs and the inability to source sufficient quantities of these molecules has led to the development of processes based on chemical synthesis to generate some of these complex molecules. However, the chemical synthesis of HMOs, as well as the enzymatic synthesis and the fermentation-based production, has proven extremely challenging. The large-scale production of HMOs with a quality sufficient for food applications has hardly been achieved thus far. In particular chemical synthesis of HMOs such as 2'-fucosyllactose (WO 2010/115935 A1) requires several noxious chemicals, which may contaminate the final product.

The drawbacks of HMO chemical synthesis have led to the development of several enzymatic and fermentation-based methods (Miyazaki et al., (2010) *Methods in Enzymol.* 480: 511-524; Murata et al., (1999) *Glycoconj. J.* 16: 189-195; Baumgartner et al. (2013) *Microb. Cell Fact.* 12: 40; Lee et al., (2012) *Microb. Cell Fact.* 11: 48; U.S. Pat. No. 7,521,212 B1; Albermann et al., (2001) *Carbohydr. Res.* 334: 97-103; Fierfort, N. and Samain, E. (2008) *J. Biotechnol.* 134: 216-265). However, these processes tend to yield complex mixtures of oligosaccharides, such that the desired product is contaminated with starting material such as lactose, as well as intermediates, unwanted by-products (e.g. by-products originating from side activities of certain glycosyltransferases) and substrates such as individual monosaccharides and polypeptides.

State of the art methods for purifying individual oligosaccharides from oligo-saccharide mixtures are technically complex, difficult to scale-up and uneconomical for food applications. Industrial-scale processes have been developed to purify the disaccharides lactose and sucrose from whey or molasses respectively, but these methods involve multiple crystallization steps which are elaborate and offer low yields. However, whey and molasses are "food grade" products to start with and nowhere near as complex and regulatory challenging as fermentation broths obtained from recombinant bacteria or recombinant yeast fermentation processes.

Gel-filtration chromatography is the best method for the purification of complex oligosaccharides such as HMOs produced by microbial fermentation, but the disadvantages of gel-filtration chromatography include its lack of scalability and its incompatibility with continuous processing. Gel-filtration chromatography is therefore uneconomical and cannot be used to produce HMOs such as 3'-sialyllactose or 6'-sialyllactose or any other sialylated oligosaccharide of sufficient quality and in sufficient quantity for human food, particularly for infant and toddler nutrition products. However, the production of sialylated HMOs (such as 3'-sialyllactose (3'-SL), 6'-sialyllactose (6'-SL), sialyllacto-N-tetraose a (LST-a), sialyllacto-N-tetraose b (LST-b), sialyllacto-N-tetraose c (LST-c), 3-fucosyl-sialyllactose (F-SL), disialyl-lacto-N-tetraose (DS-LNT) and fucosyl-LST b (F-LSTb) is interesting, because sialylated oligosaccharides are—for example—associated with improved neuronal development.

The use of recombinant microorganisms (bacteria or yeast) for fermentative production of HMOs is also problematic, because recombinant DNA or proteins could contaminate the final product, and this would not be acceptable by consumers and by regulatory authorities today. Given that detection limits in particular for recombinant DNA molecules are very low (for example when using qPCR based detection, which is currently regarded as the gold standard for detection) even as little as a single DNA molecule in an oligosaccharide product can be detected. Proteins in addition pose the risk of causing allergic reactions and should therefore be efficiently removed from the desired oligosaccharide product too.

Starting from this prior art, it was an object to provide a process for purifying sialylated oligosaccharides, in particular sialylated HMOs, that have been produced by microbial fermentation, wherein said process is applicable for commercial or industrial scale manufacturing of sialylated oligosaccharides, and which may lead to a product having a purity which renders the product suitable for human consumption.

SUMMARY

In a first aspect, provided is a method for purifying sialylated oligosaccharides that were produced by microbial fermentation or in-vitro biocatalysis.

In a second aspect, preparations of a sialylated oligosaccharides are provided that were produced by microbial fermentation or in-vitro biocatalysis.

In a third aspect, the use of the sialylated oligosaccharides according to the second aspect is provided.

In a fourth aspect, nutritional compositions comprising at least one sialylated oligosaccharide are provided, wherein said at least one sialylated oligosaccharide has been produced by microbial fermentation or in-vitro biocatalysis.

In a fifth aspect, a spray-dried, GMO-free powder is provided which consists essentially of a sialylated oligosaccharide is provided.

DETAILED DESCRIPTION

Figure 1:
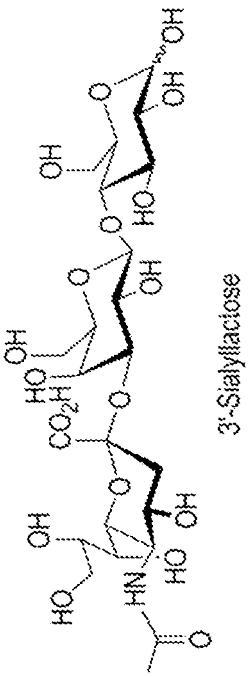
FIG. 1 displays the chemical structures of 3'-sialyllactose and 6'-sialyllactose.
Figure 1:
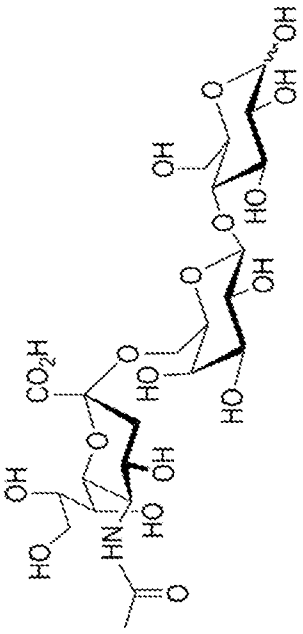

According to the first aspect, provided is a method or process for purifying sialylated oligosaccharides that were produced by microbial fermentation. The method comprises the steps of:

i) separating biomass from the fermentation broth;
ii) removing cations from the fermentation broth;
iii) removing anionic impurities from the fermentation broth; and
iv) removing compounds having a molecular weight lower than that of the sialylated oligosaccharide to be purified.

In an embodiment, the desired sialylated oligosaccharides are produced by microbial fermentation. Hence, cells being capable of producing a desired sialylated oligosaccharide are cultivated under conditions which are permissive for the cells to produce the desired sialylated oligosaccharide. Suitable cells for producing the desired oligosaccharide include bacteria, such as *Escherichia coli, Lactobacillus lactis, Corynebacterium glutamicum, Bacillus subtilis, Pseudomonas putita*, or yeasts such as *Saccharomyces cerevisiae, Schizosaccharomyces pombe, Pichia pastoris.*

The cells may be genetically engineered to produce a desired sialylated oligosaccharide a genetically not modified precursor cell is not capable of producing, or to improve production efficacy of the desired oligosaccharide. *Escherichia coli*, which is a preferred host for metabolic engineering, has been already been employed for the fermentation of HMOs (neutral HMOs as well as sialylated HMOs). However other host strains, such as yeasts (like *Saccharomyces cerevisiae*), lactic acid bacteria, *Corynebacterium glutamicum, Bacillus* species, which possess GRAS status (generally recognized as safe), might be equally well engineered for the production of oligosaccharides, HMOs in general, as well as sialylated HMOs in particular.

For the production of a desired sialylated oligosaccharide, the bacterial or yeast host strain usually contains one or more heterologous glycosyltransferases, typically at least one heterologous sialyltransferase, overexpresses genes for the synthesis of CMP-silaic acid (such as a CMP-sialic acid synthetase in addition to genes involved in the uptake or de-novo synthesis of sialic acid), a lactose importer and/or a suitable exporter for the desired sHMO. The expression of a suitable exporter is particularly advantageous when using yeast as a production hosts for sHMOs, because it is known that *S. cerevisiae* does not secrete the heterologously produced oligosaccharide in economical viable amounts into the fermentation broth without possessing a suitable exporter.

The term "desired" with respect to the sialylated oligosaccharide refers to the sialylated oligosaccharide that shall be produced by the cell. The desired sialylated oligosaccharide is the oligosaccharide to be purified by the processes disclosed herein. The term "desired" with respect to the sialylated oligosaccharide as used herein also serves to distinguish between the sialylated oligosaccharide to be produced and other sialylated oligosaccharided that may unintentionally be produced by the cells.

The term "oligosaccharide" as used herein refers to linear or branched saccharides consisting of three to 20 monosaccharide residues.

In an embodiment, the sialylated oligosaccharide is a sialylated HMO. The term "sialylated HMO" as used herein refers to human milk oligosaccharides comprising one or more sialic acid residues.

The method comprises the step of separating the biomass from the fermentation broth. This step is the first step in the process of purifying sialylated oligosaccharides.

The term "biomass" as used herein refers to the entirety of cells present in the fermentation broth at the end of the fermentation step. The cells being present in the fermentation broth at the end of the fermentation step comprise the cells being capable of producing the desired sialylated oligosaccharide, optionally auxiliary cells being present in the fermentation broth to aid in the production of the sialylated oligosaccharide such as—for example—cells which degrade undesired side products. Hence, the cells present in the fermentation broth at the end of the fermentation step are separated from the fermentation broth such that the resulting fermentation broth is substantially free of cells.

Suitable methods for separating the biomass from the fermentation broth include centrifugation wherein the biomass is obtained as pellet and the fermentation broth as supernatant. In an additional and/or alternative embodiment, the biomass is separated from the fermentation broth by means of filtration. Suitable filtration methods for separating the cells from the fermentation broth include microfiltration and ultrafiltration.

Microfiltration as such is a physical filtration process where a particle-containing fluid is passed through a special pore-sized membrane to separate the particles from the fluid. The term "microfiltration" as used herein refers to a physical filtration process where cells are separated from the fermentation broth.

Ultrafiltration is a variety of membrane filtration and is not fundamentally different. In ultrafiltration, forces like pressure or concentration gradients lead to a separation through a semipermeable membrane. Cells, suspended solids and solutes of high molecular weight are retained in the so-called retentate, while water and low molecular weight solutes such as the desired sialylated oligosaccharide pass through the membrane in the permeate (filtrate).

Ultrafiltration membranes are defined by the molecular weight cut-off (MWCO) of the membrane used. Ultrafiltration is applied in cross-flow or dead-end mode.

Suitable filters for microfiltration or ultrafiltration are SPIRA-CEL® DS MP005 4333 and fiber FS10-FC FUS1582 (Microdyn-Nadir GmbH, Wiesbaden, DE).

Typically, the cells synthesize the desired sialylated oligosaccharide intracellularly and secrete it into the fermentation broth. The thus produced sialylated oligosaccharide ends up in the fermentation broth which is then subjected to further process steps for purifying the desired sialylated oligosaccharide as described herein after.

In embodiments, where the desired sialylated oligosaccharide remains intracellularly after its biosynthesis, the biomass is separated from the fermentation broth, and said biomass is employed for purifying the desired sialylated oligosaccharide. To this end, the cells of the biomass are lysed and the resulting lysate is cleared in that insoluble constituents, nucleic acids, lipids and proteins are removed from the lysate. Methods for lysing cell and for removing insoluble constituents, nucleic acids, lipids and/or proteins from a cell lysate are known. The thus obtained cleared lysate which contains the desired sialylated oligosaccharide is then subjected to the same process steps as the cell-free fermentation broth containing the desired sialylated oligosaccharide in order to purify the desired sialylated oligosaccharide.

Notwithstanding that the process for purifying sialylated oligosaccharides is used for purifying sialylated oligosaccharides that were produced by microbial fermentation, said process may also be employed to purify sialylated oligosaccharides that were produced by an enzymatic reaction in-vitro, a so-called in-vitro biocatalysis reaction. The desired sialylated oligosaccharide is obtained by one or more enzymatic reactions in-vitro, and can be purified from the reaction mixture at the end of the biocatalytic reaction in that said reaction mixture is subjected—instead of the cell-free fermentation broth or cleared lysate—to the purification process described herein. It is understood that purifying sialylated oligosaccharides from the reaction mixture of the in-vitro biocatalysis does not require removal of biomass from the reaction mixture.

The cell-free fermentation broth, cleared lysate or reaction mixture contains the desired sialylated oligosaccharide as well as a substantial amount of impurities and undesired constituents including other oligosaccharides than the desired sialylated oligosaccharide, monovalent salts, divalent salts, amino acids, polypeptides, proteins, organic acids, nucleic acids, and monosaccharides.

The process for purifying sialylated oligosaccharides comprises the step of a cation exchange chromatography to remove positively charged compounds from the cell-free fermentation broth, the cleared lysate or the reaction mixture.

Suitable cation exchange resins for removing positively charged compounds include LEWATIT® S2568 (H+) (Lanxess AG, Cologne, DE).

The process for purifying sialylated oligosaccharides comprises the step of an anion exchange chromatography to remove undesired negatively charged compounds from the cell-free fermentation broth, cleared lysate or reaction mixture.

Suitable anion exchange resins include LEWATIT® S6368 A, LEWATIT® S4268, LEWATIT® S5528, LEWATIT® S6368A (Lanxess AG. Cologne, DE), DOWEX™ AG 1×2 (Mesh 200-400), DOWEX™ 1×8 (Mesh 100-200), Purolite CHROMALITE® CGA100×4 (Purolite GmbH, Ratingen, DE), Dow AmberLite™ FPA51 (Dow Chemicals, MI, USA).

The process for purifying sialylated oligosaccharided comprises the step of removing compounds having a molecular weight lower than that of the sialylated oligosaccharide to be purified. Suitable methods for removing compounds having a molecular weight lower than that of the sialylated oligosaccharide to be purified include nanofiltration and diafiltration.

Diafiltration involves the addition of fresh water to a solution in order to remove (wash out) membrane-permeable components. Diafiltration can be used to separate components on the basis of their molecular size and charge by using appropriate membranes, wherein one or more species are efficiently retained and other species are membrane permeable. In particular, diafiltration using a nanofiltration membrane is effective for the separation of low molecular weight compounds from salts. Nanofiltration membranes usually have a molecular weight cut-off in the range 150-300 Daltons. Nanofiltration is widely used in the dairy industry for the concentration and demineralization of whey.

Suitable membranes for nanofiltration and/or diafiltration include Dow FilmTec™ NF270-4040, TriSep® 4040-XN45-TSF (Microdyn-Nadir GmbH, Wiesbaden, DE), GE4040F30 and GH4040F50 (GE Water & Process Technologies, Ratingen, DE).

Diafiltration using nanofiltration membranes was found to be efficient as a pretreatment to remove significant amounts of contaminants prior to electrodialysis treatment of the solution containing the HMO. However, nanofiltration was found to be efficient for the removal of low-molecular-weight contaminants after an ultrafiltration step, wherein said removal is beneficial for concentrating and demineralizing the HMO solution prior to ion-exchanger treatment. The use of nanofiltration mem-branes for concentration and diafiltration during the purification of HMOs results in lower energy and processing costs, and better product quality due to reduced thermal exposure, leading to reduced Maillard reactions and aldol reactions.

The purification process provides the desired sialylated oligosaccharide in a preparation wherein the purity of said desired sialylated oligosaccharide is ≥80%, ≥85%, ≥90%, ≥95%. The process provides a preparation of the sialylated oligosaccharide wherein the purity of the sialylated oligosaccharide is suitable for food and feed applications.

Furthermore, the process is cost efficient and easy to scale up, making it suitable as a basis for a multi-ton scale manufacturing process.

The process for purifying an sialylated oligosaccharide is also advantageous in that the desired sialylated oligosaccharides are obtained free of recombinant DNA and recombinant proteins derived from recombinant microbial fermentation strains which may be used as processing aids.

In an additional and/or alternative embodiment, the process further comprises a nanofiltration step to increase the concentration of saccharides in the solution.

In an additional and/or alternative embodiment, the process comprises an electrodialysis step.

Electrodialysis combines dialysis and electrolysis, and can be used for the separation of concentration of ions in solutions based on their selective electromigration through a semipermeable membrane.

Electrodialysis (ED) combines dialysis and electrolysis and can be used for the separation or concentration of ions in solutions based on their selective electromigration through semipermeable membranes. Industrial electrodialysis applications date back to the early 1960s, when this method was used for the demineralization of cheese whey for inclusion in infant formula. Further applications of electrodialysis include the adjustment of the pH of beverages such as wines, grape must, apple juice and orange juice.

The desalination of brackish water for the production of drinking water and the demineralization of milk whey for infant food production are the most widespread applications of electrodialysis today (Tanaka, Y. (2010) Ion Exchange Membrane Electrodialysis. Nova Science Publishers, Inc. New York).

The basic principle of electrodialysis consists of an electrolytic cell comprising a pair of electrodes submerged into an electrolyte for the conduction of ions, connected to a direct current generator. The electrode connected to the positive pole of the direct current generator is the anode, and the electrode connected to the negative pole is the cathode. The electrolyte solution then supports the current flow, which results from the movement of negative and positive ions towards the anode and cathode, respectively. The membranes used for electrodialysis are essentially sheets of porous ion-exchange resins with negative or positive charge groups, and are therefore described as cationic or anionic membranes, respectively. The ion-exchange membranes are usually made of polystyrene carrying a suitable functional group (such as sulfonic acid for cationic membranes or a quaternary ammonium group for anionic membranes) cross-linked with divinylbenzene. The electrolyte can be, for example, sodium chloride, sodium acetate, sodium propionate or sulphamic acid. The electrodialysis stack is then assembled in such a way that the anionic and cationic membranes are parallel as in a filter press between two electrode blocks, such that the stream undergoing ion depletion is well separated from the stream undergoing ion enrichment (the two solutions are also referred to as the diluate (undergoing ion depletion) and concentrate (undergoing ion enrichment). The heart of the electrodialysis process is the membrane stack, which consists of several anion-exchange membranes and cation-exchange membranes separated by spacers, installed between two electrodes. By applying a direct electric current, anions and cations will migrate across the membranes towards the electrodes generating a (desalted) diluate stream and a concentrate stream.

By applying an acidic condition during electrodialysis sHMOs can be protonated such that they appear uncharged (protonation of the carbonyl group of the sialic acid part of the oligosaccharide). As an alternative, electrodialysis can be performed under neutral conditions using bipolar membranes. In this case the sialylated oligo-saccharides can be even concentrated in a separate electrodialysis concentrate circuit. Thus, sialylated Oligosaccharide can be even enriched during electrodialysis.

The pore size of the ion-exchange membranes is small enough to prevent diffusion of the product from the diluate stream into the concentrate stream, driven by high concentration differences between the two streams. After separation from biomass, proteins and in particular recombinant DNA molecules (ranging in size from fragments to entire genomes) must be quantitatively removed from the desired product. If possible at all, the electrodialysis of such large molecules (compared to the molecular size of HMOs) would take a long time, surely accompanied by significant losses of the desired product from the diluate into the concentrate.

In an additional and/or alternative embodiment, the process for purifying sialylated oligosaccharides further comprises a step of simulated bed moving (SMB) chromatography.

Simulated moving bed (SMB) chromatography originated in the petrochemical and mineral industries. Today, SMB chromatography is used by the pharmaceutical industry to isolate enantiomers from racemic mixtures. Large-scale SMB chromatography has already been used for the separation of the monosaccharide fructose from fructose-glucose solutions and for the separation of the disaccharide sucrose from sugar beet or sugar cane syrups. However, SMB chromatography has not yet been used for the purification of sialylated human milk oligosaccharides—such as sialylated lacto-N-tetraose, 3'-sialyllactose or 6'-sialyllactose during chemical, enzymatic or fermentation-based synthesis. SMB has been used to purify sialyllactoses from bovine milk, but bovine milk is a completely different matrix compared to microbial fermentation broth, which is used herein as a source of HMOs.

SMB chromatography is used as a continuous separation process analogous to continuous chemical separation processes such as rectification. In rectification, a countercurrent is established between the liquid and gas phases allowing the continuous application of feed and the continuous withdrawal of product. Counter-current chromatography should in theory achieve superior separation compared to conventional cross current systems, but the mobile and stationary phases in countercurrent systems would need to move in opposite directions. SMB chromatography was developed as a solution to the practical difficulties encountered when attempting to move a solid chromatography material in a continuous chromatographic separation process.

Figure 5:
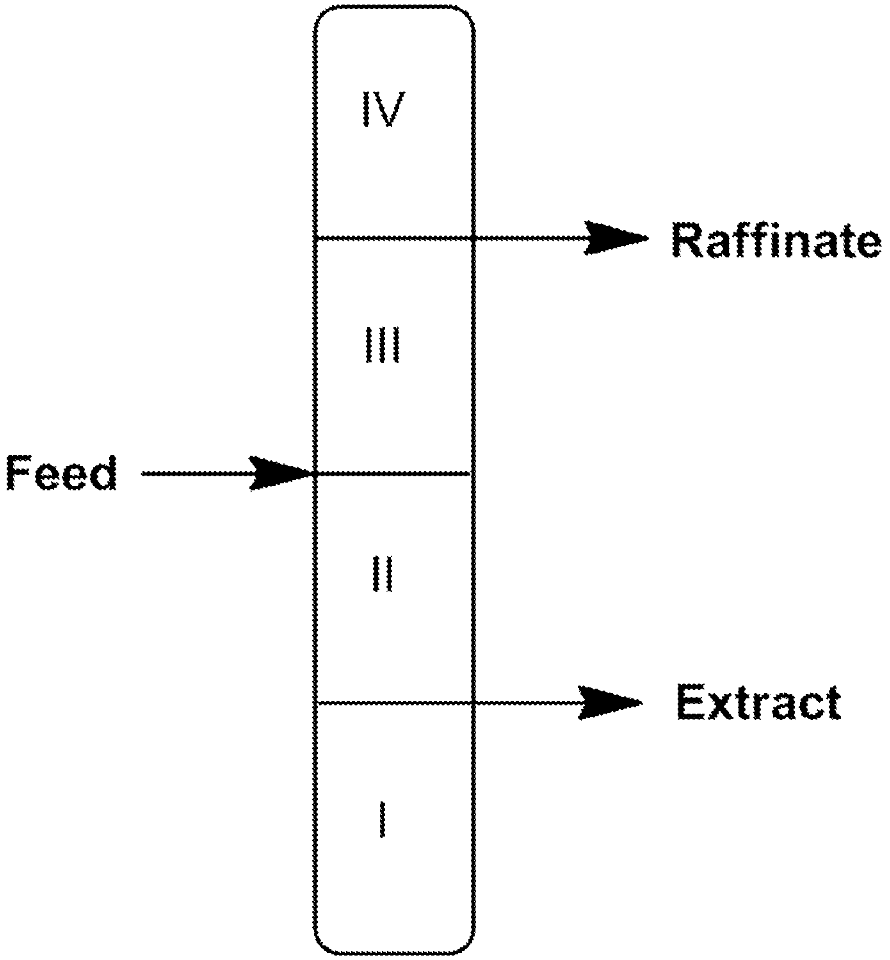
FIG. 5 illustrates the principle of a four-zone simulated moving bed chromatography.

The classical SMB concept involves four different zones with four external streams: the feed stream containing the components to be separated, the desorption or mobile-phase stream, the extract, and the raffinate stream (the latter representing the less efficiently retained components). These liquid streams divide the SMB system into four different zones (each zone or section can comprise one or more columns) with the following tasks: zone I is required for the regeneration of the solid phase, the purpose of zone II is the desorption of the less strongly desorbed material, the task of zone III is the adsorption of the strongly adsorbed material and finally the task of zone IV is the adsorption of the less adsorptive material (FIG. 5). Thus, stronger adsorbing components establish a concentration wave in zone II and are transported to the extract port whereas less strong adsorbing components migrate towards the raffinate port.

In principle, zone I and IV serve for the regeneration of the solid phase (regeneration zones) whereas zones II and III can be regarded as the actual separation zones of the system (separation zones). In addition to the four liquid streams and resulting zones, the system contains (for closed-loop operation) a recycling pump for the mobile phase (desorbent), passing the mobile phase through the fixed zones in one direction. Counter-current flow is then achieved by the periodic shifting and continuous supply or withdrawal of feed, desorbent, and products sequentially from one column to the next in the system.

In addition to the classical four-zone closed-loop 4 SMB system, three-zone open-loop systems are available, and can be more cost-effective if the fresh solvent is inexpensive, e.g. when water or water/ethanol mixtures are used as the mobile phase. In the three-zone-loop configuration, the regeneration of the liquid phase is no longer necessary, making zone IV obsolete.

Figure 6:
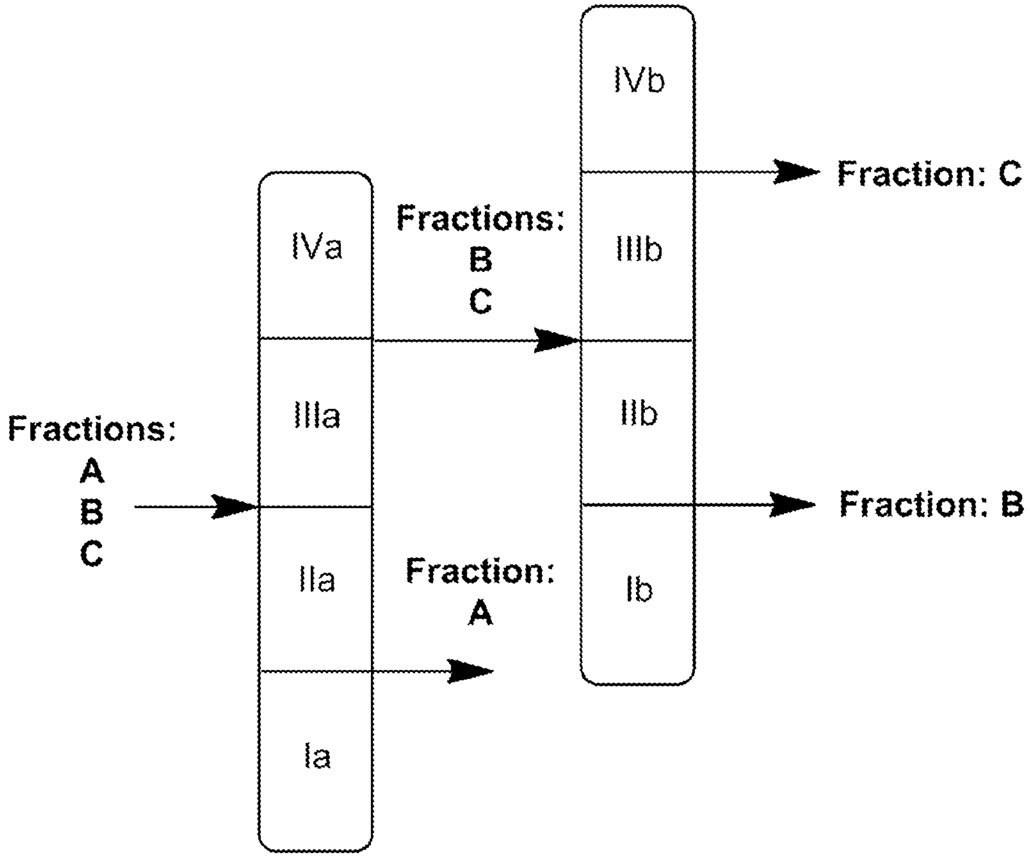
FIG. 6 illustrates the principle of an eight-zone simulated moving bed chromatography.

In addition to the classical SMB systems for the separation of two-component mixtures, eight-zone closed-loop systems (FIG. 6) and five-zone open-loop systems have been developed for the separation of more than 2 components.

Given the continuous mode of operation, the recycling of the mobile phase and also the potential to use large column sizes, SMB systems can in principle be scaled to achieve production volumes of hundreds of tons.

The process step of simulated moving bed chromatography is advantageous in that this process step allows further removal of oligosaccharides being structurally closely related to the desired sialylated oligosaccharide.

In an additional and/or alternative embodiment, the process further comprises a step of removing colorants.

Suitable process steps for removing colorants include treating the cell-free fermentation broth or the cleared lysate with activated carbon such as activated charcoal.

Treating the broth with activated carbon removes any undesired colorants and provides a preparation of the desired oligosaccharide which has an acceptable appearance.

In an additional and/or alternative embodiment, the process of purifying sialylated oligosaccharides comprises at least one step of increasing the concentration of the desired sialylated oligosaccharide.

In additional and/or alternative embodiment of the process, the solution containing the desired sialylated oligosaccharide is concentrated after at least one of the purification steps i) to iv), preferably after purification step iv), using vacuum evaporation (e.g. by using a falling film evaporator or a plate evaporator) or reverse osmosis or nanofiltration (e.g. nanofiltration with a nanofiltration membrane having a size exclusion limit of ≤20 Å)

a) to a concentration of 100 g/L, preferably 200 g/L, more preferably 300 g/L; and/or
b) at a temperature of <80° C., preferably <50° C., more preferably 20° C. to 50° C., even more preferably 30° C. to 45° C., most preferably 35° C. to 45° C. (specifically relevant for vacuum evaporation or reverse osmosis); and/or
c) at a temperature of <80° C., preferably <50° C., more preferably 4° C. to 40° C. (specifically relevant for nanofiltration).

Suitable methods for increasing the concentration of the desired sialylated oligosaccharide include nanofiltration and evaporation of solvent.

In an additional and/or alternative embodiment of the process according to the invention, the purified solution is sterile filtered and/or subjected to endotoxin removal, preferably by filtration of the purified solution through a 3 kDa filter or 6 kDa filter.

The process for purifying the desired oligosaccharide from a fermentation broth, a cell lysate or the reaction mixture of a biocatalytic reaction provides an aqueous solution of the desired oligosaccharide. In an additional and/or alternative embodiment, the process further comprises a step of removing the solvent from the sialylated oligosaccharide such that either a solution of the desired oligosaccharide is provided which includes a high concentration of the desired oligosaccharide, or such that a solid preparation of the desired oligosaccharide is obtained.

Suitable methods from removal of solvent from the liquid preparation of the sialylated oligosaccharide to obtain a solid preparation of the desired oligosaccharide include crystallization and lyophilization (freeze-drying—a process where the sHMO containing aqueous solution is frozen and then the by reducing the surrounding pressure the frozen water in the material is then allowed to sublime directly from the solid phase to the gas phase—this usually leads to a hygroscopic sHMO powder.

In an alternative embodiment, the solvent can be removed from the liquid preparation of the sialylated oligosaccharide by spray-drying. The inventors surprisingly revealed that a liquid preparation containing the desired sialylated oligosaccharide can be spray-dried to obtain a powder consisting essentially of the desired sialylated oligosaccharide, although it is well known that carbohydrates are typically not amenable to spray-drying, this also includes lactose, sialic acid, fucose etc.

Separating the biomass from the fermentation broth is typically the first step of the purification process. Provided that the process comprises the step of removing the solvent from the preparation, this step is typically the final step of purifying the desired oligosaccharide. The order of the additional process steps is not particularly limited.

Figure 2:
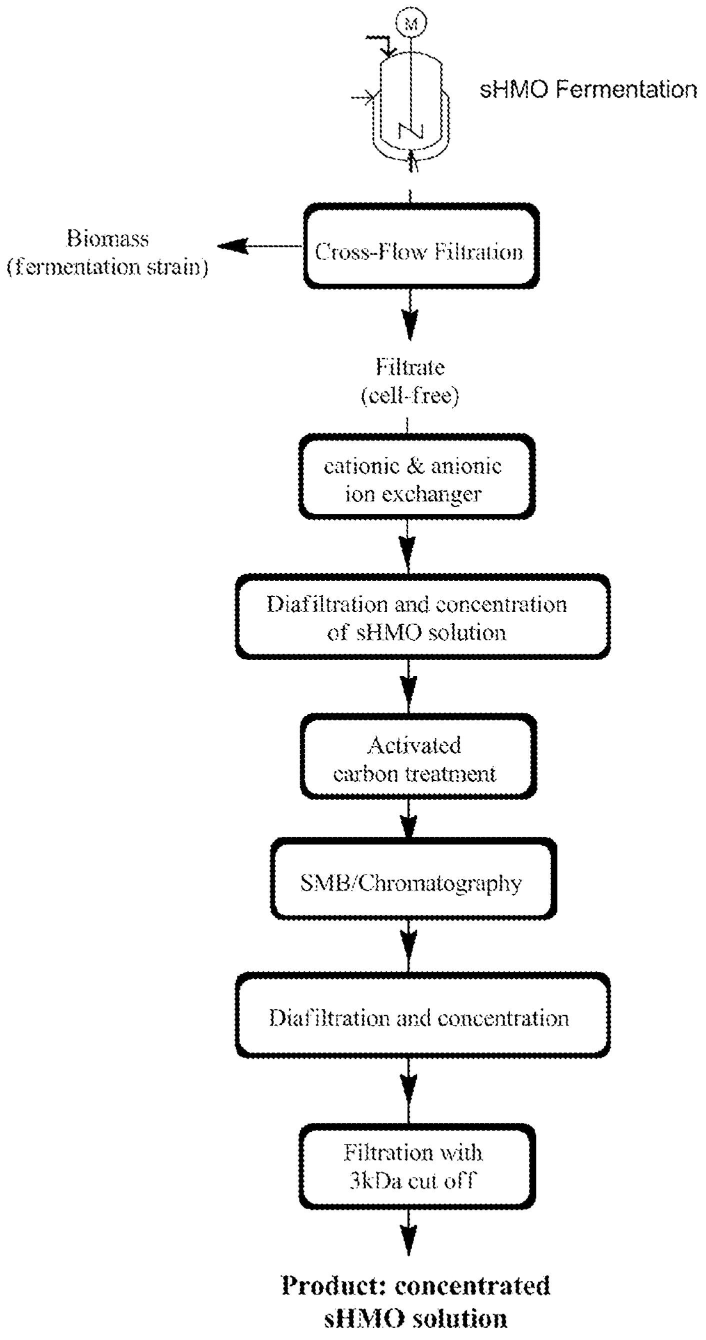
FIG. 2 shows a diagram illustrating an embodiment of the process for purifying a sialylated oligosaccharide from fermentation broth.

Referring to FIG. 2, an embodiment of the process for purifying an sialylated oligosaccharide is schematically shown, wherein the sialylated oligosaccharide is a sHMO produced by microbial fermentation. At the end of the fermentation, the biomass is separated from the fermentation broth by cross-flow filtration. The filtrate (cell-free fermentation broth) is subjected to a cation exchange chromatography and an anion exchange chromatography. Subsequently, the eluate concentrated and treated with activated carbon. The resulting solution is subjected to SMB chromatography and the concentration of the sialylated oligosaccharide in the resulting solution is increased. Finally, a filtration with a 3 kDa cut off is followed by a sterile filtration to obtain a solution containing a high concentration of the desired sHMO.

Figure 3:
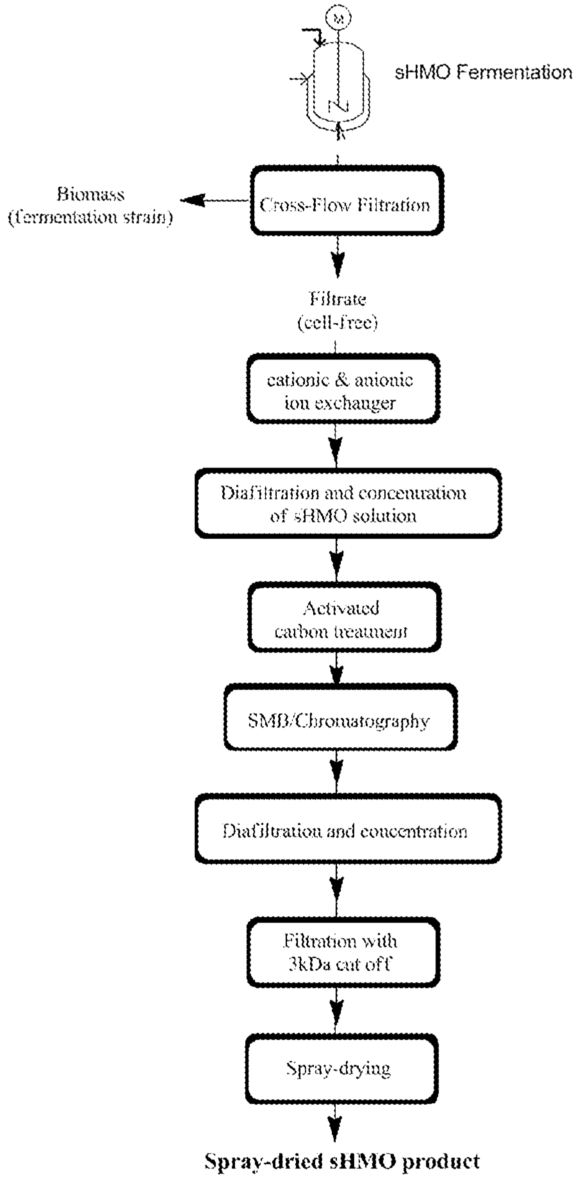
FIG. 3 shows a diagram illustrating an embodiment of the process for purifying a sialylated oligosaccharide from fermentation broth.

FIG. 3 illustrates another embodiment of the process, which differs from the embodiment shown in FIG. 2 in that the solution containing a high concentration of the desired sHMO is spray-dried to obtain the desired sHMO as powder. Unexpectedly we could identify conditions were 3'-sialyllactose and 6'-sialyllactose could be spray-dried. In contrast to lactose or sialic acid, which cannot be spray-dried, conditions could be found that allowed to obtain these sHMOs as a spray-dried powder. The spray-dried powder also appeared to be only slightly hygroscopic. The use of spray-drying has several advantages over other processes such crystallization or freeze-drying such as being highly economical, compatible to large-scale manufacturing of sHMOs, avoiding organic solvents as in the case of crystallization.

Figure 4:
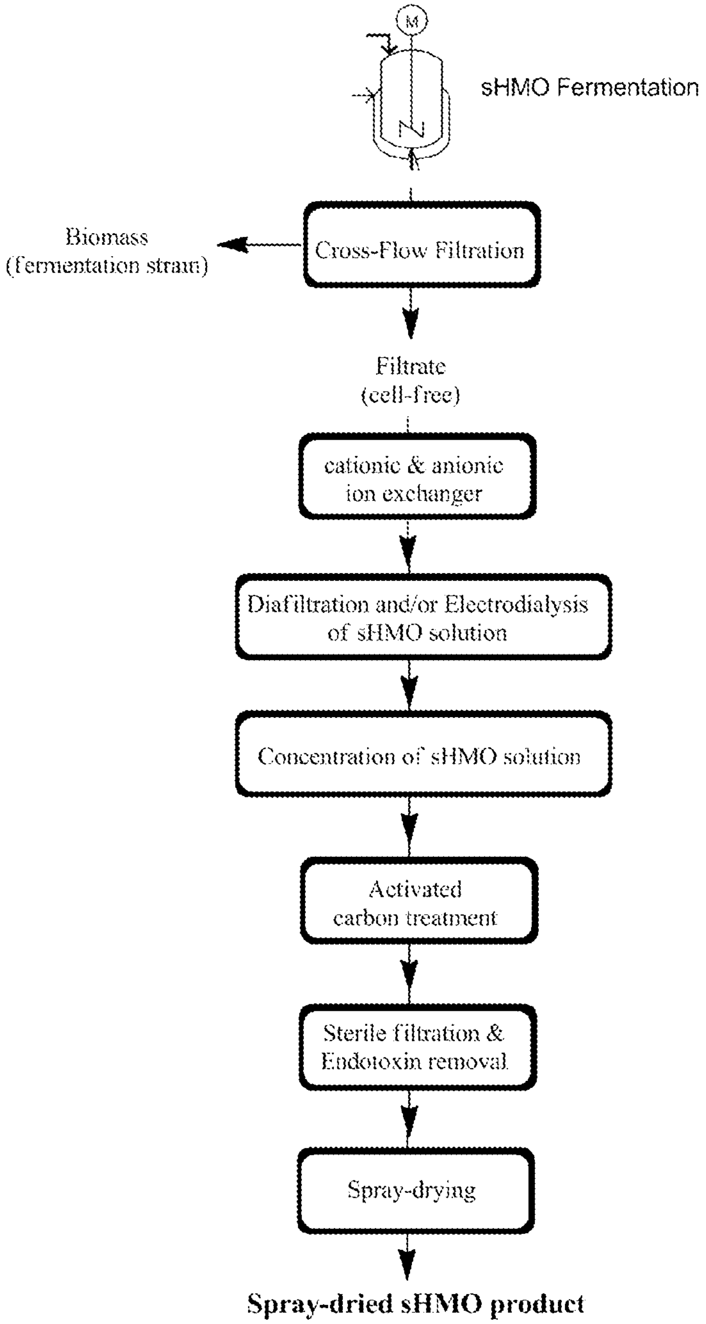
FIG. 4 shows a diagram illustrating an embodiment of the process for purifying a sialylated oligosaccharide from fermentation broth.

The embodiment of the process schematically illustrated in FIG. 4 differs from the embodiment shown in FIG. 3 in that the process does not comprise an SMB chromatography for obtaining a sHMO preparation of high purity.

According to the second aspect, provided are preparations of sialylated oligo-saccharides, wherein the sialylated oligosaccharides were produced by microbial fermentation or in-vitro biocatalysis.

The sialylated oligosaccharide of the preparation has been purified from the fermentation broth, the cells or the reaction mixture by the process described herein.

In an additional and/or alternative embodiment, the sialylated oligosaccharide is a sialylated HMO. In an additional and/or alternative embodiment, the sialylated HMO is selected from the group consisting of 3'-SL, 6'-SL, LST-a, LST-b, LST-c, F-SL, F-LST-b and DS-LNT.

The preparation of the sialylated oligosaccharide may be present in liquid form as a solution of the sialylated oligosaccharide in a solvent, preferably in water. In an alternative embodiment, the preparation of the sialylated oligosaccharide is present in solid form, preferably in form of a powder. The powder comprises the sialylated oligosaccharide in form of particles wherein the sialylated oligosaccharide is present in form of amorphous particles or in form of crystalline particles. Most preferably the sialylated oligosaccharide obtained as a spray-dried powder with a water content of less than 10%.

TABLE 1

Sialylated HMOs (sialylated human milk oligosaccharides (sHMOs) that can be purified by the method described herein.

| Name | Structure |
|---|---|
| 3'-sialyl-lactose | Neu5Ac(α2-3)Gal(β1-4)Glc |
| 6'-sialyl-lactose | Neu5Ac(α2-6)Gal(β1-4)Glc |
| F-SL | Neu5Ac(α2-3)Gal(β1-4)Glc<br>\|<br>Fuc(α1-3) |
| LSTa | Neu5Ac(α2-3)Gal(β1-3)G1cNAc(β1-3)Gal(β1-4)Glc |
| LSTb | Neu5Ac(α2-6)<br>\|<br>Gal(β1-3)GlcNAc(β1-3)Gal(β1-4)Glc |
| LSTc | Neu5Ac(α2-6)Gal(β1-4)G1cNAc(β1-3)Gal(β1-4)Glc |
| DS-LNT | Neu5Ac(α2-6)<br>\|<br>Neu5Ac(α2-3)Gal(β1-3)GlcNAc(β1-3)Gal(β1-3)Gal(β1-4)Glc |
| F-LSTb | Neu5Ac(α2-6)<br>\|<br>Fuc(α1-2)Gal(β1-3)GlcNAc(β1-3)Gal(β1-4)Glc |

The preparation of sialylated oligosaccharides obtainable by a process as described herein comprises the desired sialylated oligosaccharide in a purity of 80% by weight.

According to the third aspect, provided is the use of an sialylated oligosaccharide as described herein before, especially of a sialylated HMO, for the preparation of a nutritional composition, preferably of an infant formula.

The process of purifying sialylated oligosaccharides provides preparations of the sialylated oligosaccharides wherein the oligosaccharide is present in a purity sufficient for human consumption.

Said nutritional composition contains at least one sialylated oligosaccharide which has been produced by a method as disclosed herein before.

Thus, according to the fourth aspect, provided are nutritional compositions containing at least one sialylated oligosaccharide, preferably at least one sHMO, which has been produced by a method as disclosed herein before. The at least one sHMO in the nutritional composition is selected from the group consisting of 3'-SL, 6'-SL, LST-a, LST-b, LST-c, F-SL, DS-LNT and F-LSTb. Said at least one sialylated oligosaccharide has been produced by microbial fermentation or in-vitro biocatalysis.

In an additional embodiment, the nutritional composition is selected from the group consisting of medicinal formulations, infant formula, dairy drinks and dietary supplements. The nutritional composition further comprises micro- and/or macronutrients such as proteins, carbohydrates, fat, fatty acids, preferably polyunsaturated fatty acids (PUFAs), vitamins, minerals.

As a medicinal formulation, the nutritional composition may be used to improve the symptoms of diabetes, because sialyllactoses enhance secretion of insulin and thus increase blood glucose level for preventing or alleviating diabetes mellitus. In addition, a nutritional composition containing 3'-SL can be effective against osteoarthritis.

As infant formula, the nutritional composition meets the compositional requirements set forth in Regulation (EU) 2016/127. Exemplary compositions of infant formula are specified in Table 2 and Table 3.

TABLE 2

Components of an exemplary infant formula.

| | |
|---|---|
| Infant formula: | Skimmed milk |
| | Vegetable oils (palm oil, rapeseed oil, sunflower oil) |
| | Human milk oligosaccharides |
| | Skimmed milk powder |
| | Oil of *Mortierella alpine* |
| | Fish oil |
| | Calcium carbonate |
| | Potassium chloride |
| | Vitamin C |
| | Sodium chloride |
| | Vitamin E |
| | Iron acetate |
| | Zinc sulphate |
| | Niacin |
| | Calcium-D-panthothenate |
| | Copper sulphate |
| | Vitamin A |
| | Vitamin B1 |
| | Vitamin B6 |
| | Magnesium sulphate |
| | Potassium iodate |
| | Folic acid |
| | Vitamin K |
| | Sodium selenite |
| | Vitamin D |

TABLE 3

Composition exemplary infant formula. The final concentration is based on a preparation of 13.5 g of the powder an 90 ml of water

| | | per 100 g powder | per 100 ml infant formula |
|---|---|---|---|
| Energy | kJ | 2094-2145 | 283 |
| | kcal | 500-512 | 67-68 |
| Fat, hereof: | g | 24.2-26.2 | 3.3-3.5 |
| saturated fatty acids | g | 8.7-9.4 | 1.2-1.3 |
| monosaturated fatty acids | g | 10.4 | 1.4 |
| polyunsaturated fatty acids | g | 5.5-5.9 | 0.7-0.8 |
| Carbohydrates hereof: | g | 56-58 | 7.4-7.9 |
| Sugars hereof: | g | 44-56 | 6-7.4 |
| Lactose | g | 44-56 | 6-7.4 |
| HMOs Hereof | g | 4.22-4.81 | 0.57-0.65 |
| 2'-FL | g | 1.85-2.22 | 0.25-0.30 |
| 3-FL | mg | 555.56-592.6 | 75-80 |
| LNT | g | 1.11 | 0.15 |
| LNnT | mg | 0-111.11 | 0-15 |
| LNPF-I | mg | 0-740.74 | 0-100 |
| 3'-SL | mg | 148.15-170.37 | 20-23 |

TABLE 3-continued

Composition exemplary infant formula. The final concentration is based on a preparation of 13.5 g of the powder an 90 ml of water

| | | per 100 g powder | per 100 ml infant formula |
|---|---|---|---|
| 6'-SL | mg | 207.4-222.22 | 28-30 |
| Protein | g | 11.11-11.85 | 1.5-1.6 |
| Salt | g | 0.47-0.59 | 0.06-0.08 |
| Vitamins | | | |
| Vitamin A | µg | 357-358 | 47.3-48.2 |
| Vitamin D | µg | 7.8 | 1.05 |
| Vitamin E | mg | 8.1.5 | 1.1 |
| Vitamin K | µg | 43.7-44.4 | 5.9-6.0 |
| Vitamin C | mg | 115-118 | 15-16 |
| Vitamin B1 | mg | 0.51-0.60 | 0.068-0.079 |
| Vitamin B2 | mg | 1.3-1.7 | 0.18-0.23 |
| Niacin | mg | 3.63 | 0.49 |
| Vitamin B6 | µg | 526-600 | 71-81 |
| Folic acid | µg | 160-164 | 21.6-21.7 |
| Vitamin B12 | µg | 1.7-1.9 | 0.23-0.25 |
| Biotin | µg | 22-30 | 3.0-3.9 |
| Panthothenic acid | mg | 4.6-5.4 | 0.62-0.72 |
| Minerals | | | |
| Sodium | mg | 187-236 | 25.3-31.2 |
| Potassium | mg | 673-675 | 88.8-91.2 |
| Chloride | mg | 327-33 | 43.1-44.9 |
| Calcium | mg | 460-504 | 62.1-66.5 |
| Phosphorous | mg | 335-352 | 45.2-46.5 |
| Magnesium | mg | 49.3-56.3 | 6.66-7.43 |
| Iron | mg | 4.15 | 0.56 |
| Zinc | mg | 3.7-3.8 | 0.49-0.51 |
| Copper | µg | 274 | 37 |
| Manganese | µg | 96.3 | 13 |
| Fluoride | µg | 30.4-32.6 | 4.1-4.4 |
| Selenium | µg | 11.1-12.3 | 1.5-1.6 |
| Iodine | µg | 101.5-103.7 | 13.7-14 |

In an additional and/or alternative embodiment, the nutritional composition further comprises microorganisms, preferably probiotic microorganisms. In case when used for infant food applications, preferred microorganisms are derived from or can be found in the microbiome of a healthy human. Preferably, but no limited to, the microorganisms are selected from the genera *Bifidobacterium, Lactobacillus, Enterococcus, Streptococcus, Staphylococcus, Peptostreptococcus, Leuconostoc, Clostridium, Eubacterium, Veilonella, Fusobacterium, Bacterioides, Prevotella, Escherichia, Propionibacterium* and *Saccharomyces*. In an additional and/or alternative embodiment, the microorganism is selected from the group consisting of *Bifidobacterium breve, Bifidobacterium longum, Bifidobacterium lactis, Bifidobacterium animalis, Bifidobacterium bifidum, Bifidobacterium infantis, Bifidobacterium aldolescentis, Lactobacillus acidophilus, Lactobacillus plantarum, Lactobacillus salivarius, Lactobacillus casei, Lactobacillus gasseri, Lactobacillus reuteri, Lactobacillus rhamnosus, Lactobacillus plantarum, Lactobacillus salivarius, Lactococcus lactis, Lactobacillus paracasei, Lactobacillus bulgaricus, Lactobacillus helveticus, Lactobacillus fermentum, Leuconostoc mesenteroides; Escherichia coli, Enterococcus faecium*, and *Streptococcus thermophilus* (VSL #3).

In addition to the combination of sHMOs with living organisms, these oligosaccharides can be also used in combination with dead cultures. In the field of probiotics sometimes killed cultures are used (e.g. tyndalized bacteria). It is believed that these killed cultures provide proteins, peptides, oligosaccharides, cell outer wall fragments, natural products, which can lead to a short term stimulation of the immune system.

The combination of at least one sialylated oligosaccharide, in particular at least one sHMO, and probiotic microorganisms in the nutritional composition is particularly advantageous in that establishing or re-establishing an appropriate microbiome in the gut, and the health benefits associated therewith is facilitated.

Even more advantageous is the combination of at least one sialylated oligosaccharide, in particular one sHMO, with established prebiotics such as GOS (Galactooligosaccharides) and/or FOS (Fructooligosaccharides, Inulin).

The nutritional composition may be present in liquid form or in solid form including, but not limited to, powders, granules, flakes and pellets.

Thus, provides is also a nutritional composition comprising at least 5 HMOs, wherein said at least 5 HMOs are selected form the group consisting of 2'-Fucosyllactose, 3-Fucosyllactose, Lacto-N-tetraose, Lacto-N-neotetraose, Lacto-N-fucopentaose I, 3'-Sialyllactose and 6'-Sialyllactose.

In an additional and/or alternative embodiment, a nutritional composition as disclosed herein before contains at least one sialylated HMO and at least one neutral HMO and a probiotic microorganism.

According to the fifth aspect, a spray-dried, GMO-free powder is provided which consists essentially of a sialylated oligosaccharide with a purity of >80% by dry-weight and possessing less than 10% water by weight.

In an embodiment, the spray-dried powder is a powder consisting essentially of a sialylated oligosaccharide selected from the group consisting of 3'-sialyllactose, 6'-sialyllactose, and a mixture of 3'-sialyllactose and 6'-sialyllactose.

In an additional and/or alternative embodiment the spray-dried powder essentially consists of a mixture of 3'-sialyllactose, 6'-sialyllactose and one or more neutral HMOs, wherein said one or more neutral HMOs being selected from the group consisting of 2'-fucosyllactose, 3-fucosyllactose, lacto-N-tetraose, lacto-N-neotetraose, lacto-N-fucopentaose I.

The present invention will be described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Example 1: Fermentation of 3'-Sialyllactose Using a Recombinant Microorganism A 3'-sialyllactose fed-batch fermentation employing a recombinant 3'-sialyllactose synthesizing *E. coli* strain (*E. coli* BL21(DE3) dlacZ), containing a genomic integration of a 3'-sialyltransferase gene from *Vibrio* sp. JT-FAJ-16. To enhance the biosynthesis of CMP-sialic acid genes encoding the glucosamine-6-phosphate synthase GlmS from *E. coli*, the N-acetylglucosamin2-epimerase Slr1975 from *Synechocystis* sp., the glucosamine 6-phosphat N-acetyltransferase Gna1 from *Saccharomyces cerevisiae*, the phosphoenolpyruvat synthase PpsA from *E. coli*, the N-acetylneuraminate synthase NeuB, and the CMP-sialic acid synthetase NeuA, the latter both from *Campylobacter jejuni*, were chromosomally integrated into the *E. coli* BL21(DE3) host. Furthermore, the gene encoding the lactose permease LacY from *E. coli*, and the genes cscB (sucrose permease), cscK (fructokinase), cscA (sucrose hydrolase), and cscR (transcriptional regulator) from *E. coli* W were integrated into the BL21 genome. Transcription of integrated genes is initiated from constitutive promotors, either the tetracycline promotor $P_t$et or the $P_{T5}$ promotor. A functional gal-operon, consisting of the genes galE (UDP-glucose-4-epimerase), gaiT (galactose-1-phosphate uridylyltransferase), ga/K (galactokinase), and ga/M (galactose-1-epimerase) was transferred from *E. coli* K12 to the genome of the BL21 strain. To prevent degradation of N-acetylglucosamine 6-phosphate genes coding for the N-acetylglucosamine-6-phosphate deacetylase (NagA), the glucosamine-6-phosphate deaminase (NagB), and the N-acetylglucosamine specific PTS protein IIABC (NagE) were deleted from the chromosome. Additionally, the operon manXYZ, encoding a sugar transporter of the *E. coli* PTS system for mannose, glucose, glucosamine and N-acetylglucosamine was deleted, as well as the genes nanA, nanK, nanE, and nanT, encoding the N-acetylneuraminate lyase, the N-acetylmannosamine kinase, the N-acetylmannosamine-6-phosphate epimerase, and the sialic acid transporter, respectively. The gene encoding the N-acetylgalactosamine-6-phosphate deacetylase (AgaA) was also deleted.

The 3'-sialyllactose producing strain was grown in a defined mineral salts medium, comprising 7 g $l^{-1}$ $NH_4H_2PO_4$, 7 g $l^{-1}$ $K_2HPO_4$, 2 g $l^{-1}$ KOH, 0.3 g $l^{-1}$ citric acid, 5 g $l^{-1}$ $NH_4Cl$, 1 ml $l^{-1}$ antifoam (Struktol J673, Schill+Seilacher), 0.1 mM $CaCl_2$, 8 mM $MgSO_4$, trace-elements and 2% sucrose as carbon source.

Trace elements consisted of 0.101 g $l^{-1}$ nitrilotriacetic acid, pH 6.5, 0.056 g $l^{-1}$ ammonium ferric citrate, 0.01 g $l^{-1}$ $MnCl_2$×4 $H_2O$, 0.002 g $l^{-1}$ $CoCl_2$×6 $H_2O$, 0.001 g $l^{-1}$ $CuCl_2$×2 $H_2O$, 0.002 g $l^{-1}$ boric acid, 0.009 g $l^{-1}$ $ZnSO_4$×7 $H_2O$, 0.001 g $l^{-1}$ $Na_2MoO_4$×2 $H_2O$, 0.002 g $l^{-1}$ $Na_2SeO_3$, 0.002 g $l^{-1}$ $NiSO_4$×6 $H_2O$.

The sucrose feed (500 g $l^{-1}$) was supplemented with 8 mM $MgSO_4$, 0.1 mM $CaCl_2$, trace elements, and 5 g $l^{-1}$ $NH_4Cl$. For 3'-sialyllactose formation, a lactose feed of 216 g $l^{-1}$ was employed. The pH was controlled by using ammonia solution (25% v/v). Fed batch fermentation was conducted at 30° C. under constant aeration and agitation for 72 hours by applying a sucrose feeding rate of 5.5-7 mL $L^{-1}$ $h^{-1}$, referring to the starting volume. At 72 hours after the start of the fermentation, most of the added lactose was converted into 3'-sialyllactose. In order to remove residual lactose in the fermentation supernatant, 3-galactosidase was added to the fermentation vessel. The resulting monosaccharides were metabolized by the production strain.

Example 2: Fermentation of 6'-Sialyllactose a sHMO Using a Recombinant Microorganism The strain synthesizing 6'-sialyllactose comprises the same genetic features like the 3'-sialyllactose producing strain, despite the sialyltransferase. For the production of 6'-sialylactose the plsT6 gene from *Photobacterium leiognathi* JT-SHIZ-119 encoding an alpha-2,6-sialyltransferase was integrated into the *E. coli* BL21(DE3) genome.

For the fermentative production of 6'-sialyllactose the strain was grown in a defined mineral salts medium, comprising 7 g $l^{-1}$ $NH_4H_2PO_4$, 7 g $l^{-1}$ $K_2HPO_4$, 2 g $l^{-1}$ KOH, 0.3 g $l^{-1}$ citric acid, 5 g $l^{-1}$ $NH_4Cl$, 1 ml $l^{-1}$ antifoam (Struktol J673, Schill+Seilacher), 0.1 mM $CaCl_2$, 8 mM $MgSO_4$, trace-elements (0.101 g $l^{-1}$ nitrilotriacetic acid, pH 6.5, 0.056 g $l^{-1}$ ammonium ferric citrate, 0.01 g $l^{-1}$ $MnCl_2$×4 $H_2O$, 0.002 g $l^{-1}$ $CoCl_2$×6 $H_2O$, 0.001 g $l^{-1}$ $CuCl_2$×2 $H_2O$, 0.002 g $l^{-1}$ boric acid, 0.009 g $l^{-1}$ $ZnSO_4$×7 $H_2O$, 0.001 g $l^{-1}$ $Na_2MoO_4$×2 $H_2O$, 0.002 g $l^{-1}$ $Na_2SeO_3$, 0.002 g $l^{-1}$ $NiSO_4$×6 $H_2O$) and 2% sucrose as carbon source.

The sucrose feed (500 g $l^{-1}$) was supplemented with 8 mM $MgSO_4$, 0.1 mM $CaCl_2$, trace elements, and 5 g $l^{-1}$ $NH_4Cl$. For 6'-sialyllactose formation, a lactose feed of 216 g $l^{-1}$ was employed. The pH was controlled by using ammonia solution (25% v/v). Fed batch fermentation was conducted at 30° C. under constant aeration and agitation for 72 hours by applying a sucrose feeding rate of 5.5-7 mL $L^{-1}$ $h^{-1}$, referring to the starting volume. Lactose that was not converted into 6'-sialyllactose at the end of the production process was degraded by addition of 3-galactosidase and monosaccharides from hydrolysis of lactose were metabolized by the production strain.

Example 3: Purification of 6'-Sialyllactose and 3'-Sialyllactose from Fermentation Broth The biomass was separated from the fermentation medium by ultrafiltration followed by using sequentially a winding module filter (0.05 μm cut-off) (CUT membrane technology, Erkrath, Germany), and a cross-flow filter (150 kDa cut-off) (Microdyn-Nadir, Wiesbaden, Germany). An approximately 1 $m^3$ cell-free fermentation medium was obtained containing more than 20 g $L^{-1}$ sialylated oligosaccharides.

The cell-free liquid was then deionized by ion exchange chromatography. First, cationic contaminants were removed on a strong cationic exchanger in a volume of 200 L (LEWATIT® S 2568 (Lanxess, Cologne, Germany) in $H^+$ form. Using NaOH the pH of the obtained solution was set to 7.0. In a second step, anionic ions and undesired colorants were removed from the solution using the strong anionic exchanger LEWATIT® S 6368 S (Lanxess, Cologne, Germany) in the chloride form. The ion exchanger had a bed volume of 200 L. Using a second filtration step on the cross-flow filter (150 kDa cut-off) (Microdyn-Nadir, Wiesbaden, Germany), precipitates originating from acidifying the solution were removed. For concentration of the sugar, the solution was nanofiltered on a Dow FilmTec® NF270-4040 (Inaqua, Mönchengladbach, Germany), or, alternatively on a TriSep® 4040-XN45-TSF Membrane (0.5 kDa cut-off) (Microdyn-Nadir, Wiesbaden, Germany). Using the latter, the monosaccharide N-acetylglucosamine, originating from the fermentation process and contaminating the sialyllactose solution, was separated from the product. The concentrated sialyllactose solution was then treated with activated charcoal (CAS:7440-44-0, Carl Roth, Karlsruhe, Germany) to remove colorants such as Maillard reaction products and aldol reaction products. In order to separate the sialyllactose from by-products that originate from the fermentation process like sialic acid and N-acetylglucosamine, the solution was filtrated on with a 1 kDa cut-off membrane GE4040F30 (GE water & process technologies, Ratingen, Germany), and diafiltrated to a conductivity of 0.6 to 0.8 mS. The diluted solution was concentrated on a rotary evaporator to a concentration of about 300 g $L^{-1}$. In a final chromatographic separation other contaminating sugars, like di-sialyllactose were removed. Therefor the concentrated solution was applied to a weak anion ion exchange resin in the acetate form (AmberLite™ FPA51, Dow Chemical, Michigan, USA). While the sialyllactose rarely binds to the resin, the di-sialyllactose is adsorbed. Thus, the sialyllactose is eluted with 10 mM ammonium acetate, while the di-sialyllactose is eluted with 1 M ammonium acetate. For removal of the ammonium acetate, the sialyllactose was precipitated with a 10-fold excess of ethanol. The solid fraction was filtrated and dried.

The product was finalized by passing a 20% sialyllactose solution sequentially through a 6 kDa filter (Pall Microza ultrafiltration module SIP-2013, Pall Corporation, Dreieich, Germany) and a 0.2 μm sterile filter.

A part of the solution was spray dried using a Büchi spray dryer (Büchi Mini Spray Dryer B-290) (Büchi, Essen, Germany), applying the following parameters: Inlet-temperature: 130° C., Outlet temperature 67° C.-71° C., gas flow 670 L/h, aspirator 100%.

The spray-dried 6'-sialyllactose had a purity of 91%, while the 3'-sialyllactose material had a purity of 93%.

Example 4: Analysis of the Spray Dried Sialyllactoses by Wide Angle X-Ray Power Diffraction (XDR)

Wide angle X-ray powder diffraction (XRD) was used to study the morphology of lyophilized products. The X-ray diffractometer Empyrean (Panalytical, Almelo, The Netherlands) equipped with a copper anode (45 kV, 40 mA, $K_a$ emission at a wavelength of 0.154 nm) and a PIXcel3D detector was used. Approximately 100 mg the spray-dried samples were analyzed in reflection mode in the angular range from 5-45° 2θ, with a step size of 0.04° 2θ and a counting time of 100 seconds per step.

Figure 7:
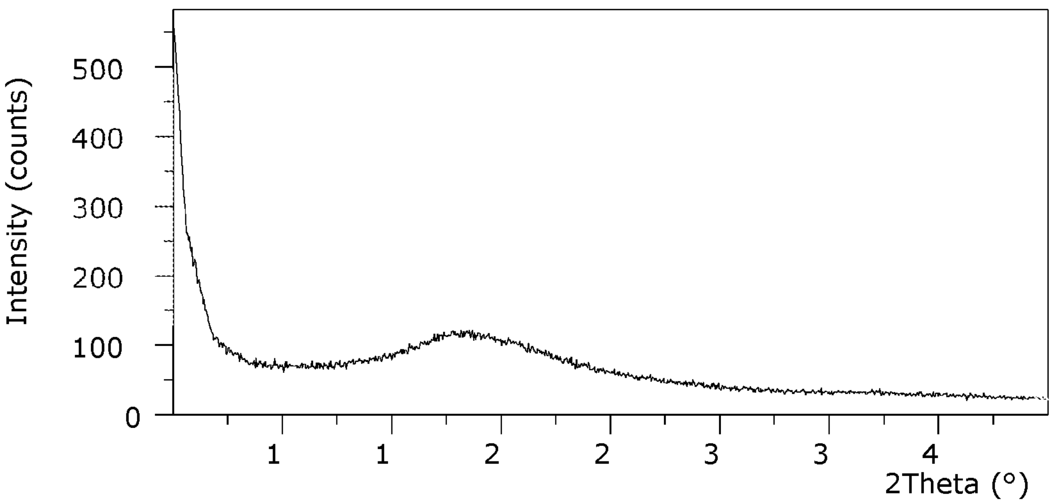
FIG. 7 shows a graph illustrating the results of a X-ray powder diffraction of spray-dried 6'-SL.
Figure 8:
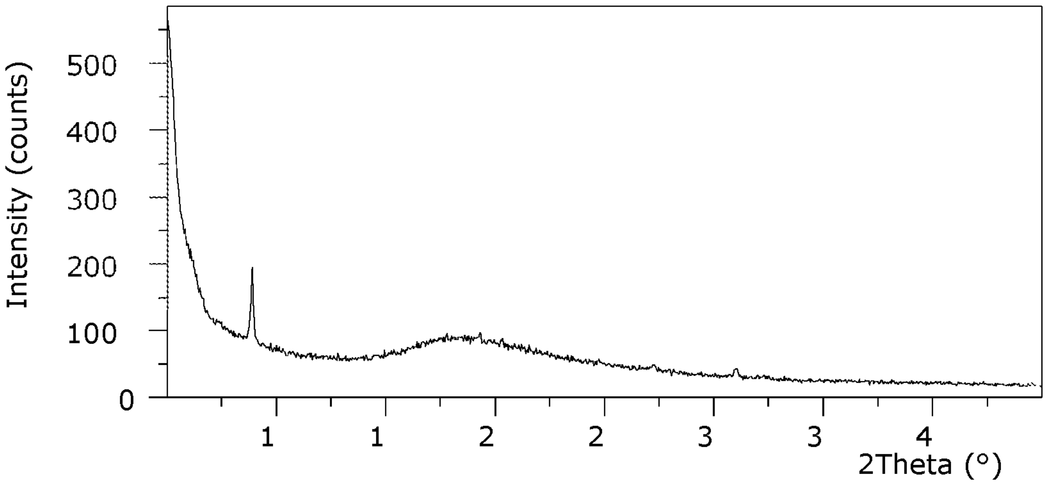
FIG. 8 shows a graph illustrating the results of a X-ray powder diffraction of spray dried 3'-SL.

Spray dried 6'-Sialyllactose was found to have a fully amorphous structure (FIG. 7), whilst the sample of the 3'-sialyllactose shows two diffraction peaks, at 7° and 31°, indicating a partly crystalline structure, however, also the 3'-sialyllactose sample gives predominantly an amorphous signal (FIG. 8).

Example 5: Analysis of the Spray Dried Sialyllactoses by Differential Scanning Calorimetry (DSC)

Differential scanning calorimetry (DSC) in a Mettler Toledo™ 821e (Mettler Toledo, Giessen, Germany) was used to determine thermal events of the spray-dried products (glass transition temperature (Tg), further exo- and endothermic events).

Approximately 25 mg of the spray-dried product was analyzed in crimped Al-crucibles (Mettler Toledo™, Giessen, Germany). The samples were cooled to 0° C. with 10 K/min and reheated to 100° C. with a scanning rate of 10 K/min. After cooling down the samples to 0° C. in a second heating cycle the samples were heated to 150° C. The midpoint of the endothermic shift of the baseline during the heating scan was taken as Tg. Exothermic and endothermic peaks are reported by means of the peak temperature and the normalized energy of the event.

The sample of spray dried 6'-sialyllactose exhibited a Tg value of 48° C. in the first heating scan, and a Tg of 50° C. in the second heating scan with an endothermal relaxation peak after the first Tg. Compared to the 6'-sialyllactose showed the 3'-sialyllactose Tg values of 22° C. in both heating scans, indicating a higher stability of the 6'-sialyllactose at higher temperatures.

The invention claimed is:

1. A spray-dried, GMO-free powder consisting essentially of a sialylated oligosaccharide with a purity of >80% by dry-weight and possessing less than 10% water by weight, wherein the sialylated oligosaccharide has been produced by microbial fermentation, wherein the sialylated oligosaccharide is present in the form of amorphous particles and predominantly shows no diffraction peaks between 5-45° by wide angle x-ray power diffraction and wherein the spray-dried powder is capable of being formulated into a nutritional composition selected from a medicinal formulation, a dietary supplement, a dairy drink, and an infant formula.

2. The spray-dried powder of claim 1, wherein the sialylated oligosaccharide is 3'-sialyllactose.

3. The spray-dried powder of claim 1, wherein the sialylated oligosaccharide is 6'-sialyllactose.

4. The spray-dried powder of claim 1, wherein the sialylated oligosaccharide is a mixture of 3'-sialyllactose and 6'-sialyllactose.

5. The spray-dried powder of claim 1, further comprising one or more neutral HMOs, wherein the one or more neutral HMOs are selected from 2'-fucosyllactose, 3-fucosyllactose, lacto-N-tetraose, lacto-N-neotetraose, and lacto-N-fucopentaose I.

6. The spray-dried powder of claim 2, wherein the sialylated oligosaccharide in the form of amorphous particles shows a glass transition temperature (Tg) of ≥20° by differential scanning calorimetry.

7. The spray-dried powder of claim 3, wherein the sialylated oligosaccharide in the form of amorphous particles shows a glass transition temperature (Tg) of ≥45° by differential scanning calorimetry.

* * * * *